May 26, 1942. H. C. SWIM Plant Pat. 524

ROSE PLANT

Filed Oct. 21, 1941

INVENTOR
H. C. SWIM
BY Robb & Robb.
ATTORNEYS

Patented May 26, 1942

UNITED STATES PATENT OFFICE

524

ROSE PLANT

Herbert C. Swim, Ontario, Calif., assignor to Armstrong Nurseries, Inc., Ontario, Calif., a corporation of California Application October 21, 1941, Serial No. 415,961

1 Claim. (Cl. 47—61)

The present discovery relates to a new and distinct variety of rose plant, originating as a bud sport of the rose "Picture" found by me in the growing fields of Armstrong Nurseries, Inc., at Ontario, California.

The most clearly distinguishing features of this new rose are its vigorous growing or climbing habit, characterized by its strong canes attaining a height of twelve to fourteen feet or more as compared with the usual height of three or four feet attained by the bush form of the rose "Picture" when grown under comparable conditions; its habit of producing many more flowers in the spring than can be found at any one time on the bush variety "Picture"; and its intermittent flowering during the rest of the season.

In addition to the above distinctions, the flowers of this new variety are usually larger in size and greater in petalage than the flowers found on the bush "Picture," there being from seven to twelve more petals. No novelty of the bud or blossom is claimed.

This new variety has been asexually reproduced over a period of years and these characteristics above noted have proved to be permanently fixed through budding and grafting.

Figure 1:
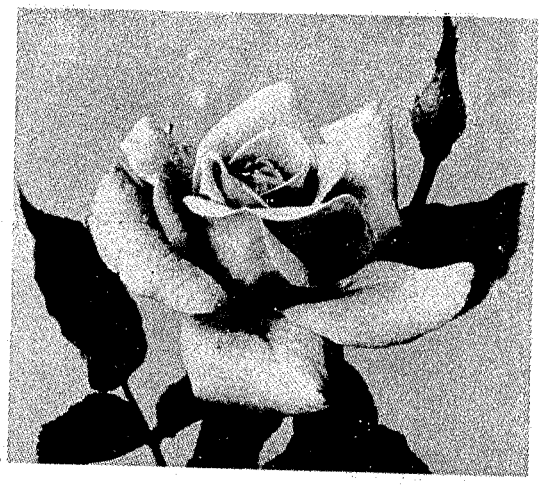
Figure 2:
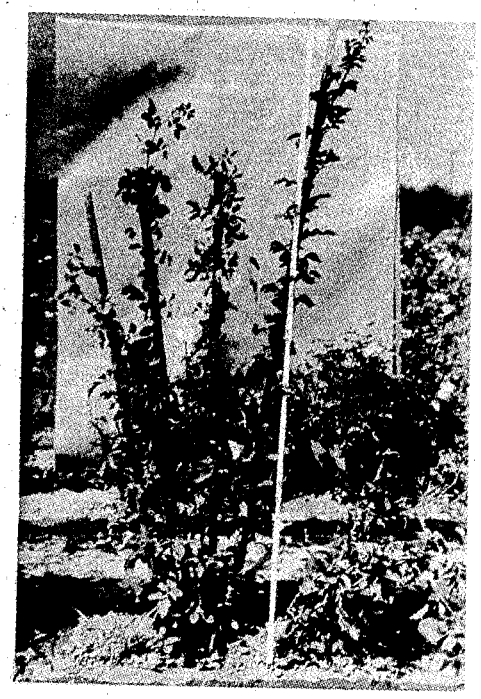

The illustration accompanying this application shows in Figure 1 one year's growth of a specimen of this new variety of rose plant together with a yardstick set up beside it to indicate its vigorous climbing growth. In Figure 2 of the drawing is illustrated a specimen flower of this variety.

The following is a detailed description of the plant and flower of this new variety of rose plant, all color terminology being in accord with Ridgway's Color Standard:

Type: Tender to half hardy; tall; climbing; sport; for cut flowers and garden decoration.

Class: Hybrid tea—climbing.

Breeding or discovery: Sport.

*Parent.*—"Picture." A climbing branch discovered on bush rose variety "Picture."

Propagation: Holds its distinguishing characteristics through succeeding propagations by grafting and budding.

*Flower*

Locality where grown: Ontario, California.

Flowers borne: Usually singly, sometimes two or more to stem; in irregular cluster; on strong, medium to long stems.

Quantity of bloom: Abundant outdoors.

Continuity: One season to intermittent.

Fragrance: Moderate; spicy.

Bud:

*Pedicel.*—Medium to long; medium heavy; erect; stiff; almost smooth with numerous gland-tipped cilia; near Biscay Green Plate XVII, before calyx breaks; near Courge Green, Plate XVII, as calyx breaks.

*Before calyx breaks.*—*Size*—medium. *Form*—Moderately long; pointed, with a conspicuous neck; with foliaceous appendages with tomentum and gland-tipped cilia on the surface of the bud; with slender, bristle-like foliaceous parts extending beyond the tip of the bud equal to one-half or more of its length.

*As calyx breaks.*—Outside of petal—between Pompeian Red, Plate XIII, and Jasper Red, Plate XIII, with shadings or blendings of near Light Coral Red, Plate XIII, near base of petal and sometimes at tip of petal. Inner surface of sepal—with fine, woolly tomentum. The margins of two sepals are lined with woolly tomentum; two other sepals are lined with stipitate glands; the fifth sepal has one margin lined with woolly tomentum and the other margin lined with stipitate glands.

*As first petal opens.*—*Size*—medium. *Form*—ovoid. *Color.*—outside—between Spinel Red, Plate XXVI, and Begonia Rose, Plate I, at edge of border blending gradually to between Begonia Rose, Plate I, and Strawberry Pink, Plate I, toward the center and base of the petal, changing abruptly at point of attachment to near Green Yellow, Plate V. Inside—between Rose Red, Plate XII, and Begonia Rose, Plate I, around border of petal blending gradually near Begonia Rose toward center of petal which in turn blends gradually to between Begonia Rose and Strawberry Pink, Plate I, toward base of petal, which in turn changes abruptly to near Lemon Yellow, Plate IV, at point of attachment. On close observation a very thin pencil-line margin of between Geranium Pink, Plate I, and Eosine Pink, Plate I, may be seen. *Opening*—opens up well.

Bloom:

*Size.*—When fully open—medium; 3¼ inches to 3¾ inches.

*Petalage.*—Semi-double; from 25 to 30 petals; arranged irregularly.

*Form.*—High center at first; becoming cupped; petals remaining at first loosely rolled outward; becoming later, at maturity, usually loosely but sometimes tightly rolled outward.

Petals: Moderately thick and soft; with inside velvety and outside satiny.

*Shape.*—Outside—round to broadly obovate; usually with mucronate tip; scalloped sometimes with one, two, three or more notches. Intermediate—Broadly obovate; mucronate; sometimes scalloped with one, two or three notches, but usually not notched. Inside—Broadly obovate; scalloped irregular with one, two or three or more notches.

*Color.*—Colors may be modified by being faintly margined, shaded and washed with other colors.

This description of a newly opened flower was made from a rose grown outdoors in the month of August, 1941, at Ontario, California:

*Color.*—Outside petal: Outside surface—Between Eosine Pink, Plate I, and Thulite Pink, Plate XXVI, at tip of petal blending gradually to between Eosine Pink and Begonia Rose, Plate I, which in turn changes gradually to near Rose Doree, Plate I, at base of petal, which changes abruptly at point of attachment to between Pale Lemon Yellow, Plate IV, and Light Green Yellow, Plate V; inside surface—between Eosine Pink, Plate I, and Thulite Pink, Plate XXVI, at tip blending gradually to between Eosine Pink, Plate I, and Begonia Rose, Plate I, toward lower half of petal which in turn blends gradually to between Rose Doree, Plate I, and Strawberry Pink, Plate I, toward point of attachment, changing abruptly at point of attachment to near Pale Lemon Yellow, Plate IV. On close observation a fine pencil-line margin of near Hermosa Pink, Plate I, may be seen almost entirely bordering the petal. Intermediate petal: outside surface—near Begonia Rose, Plate I, with a very faint washing or overtone of near Spinel Pink, Plate XXVI (however, near Begonia Rose is predominant), at tip of petal blending gradually to between Begonia Rose, Plate I, and Rose Doree, Plate I, at base of petal, changing abruptly to between Pale Lemon Yellow, Plate IV, and Light Green Yellow, Plate V, at point of attachment; Inside surface—between Begonia Rose, Plate I, and Spinel Pink, Plate XXVI, blending gradually to between Begonia Rose, Plate I, and Rose Doree, Plate I, at base changing abruptly to near Pale Lemon Yellow, Plate IV at point of attachment. On close observation, a fine pencil-line margin of near Hermosa Pink, Plate I, may be seen bordering the petal. Inner petal: outside surface—between Rose Red, Plate XII, and Spinel Red, Plate XXVI, at tip blending quickly between Rose Red, Plate XII, and Begonia Rose, Plate I, which in turn blends gradually to between Begonia Rose, Plate I, and Rose Doree, Plate I, toward base of petal changing abruptly at point of attachment to between Picric Yellow, Plate IV, and Light Greenish Yellow, Plate V; inside surface—near Rose Red, Plate XII, blending very gradually to between Begonia Rose, Plate I, and Rose Doree, Plate I, toward base of petal, changing abruptly to near Lemon Yellow, Plate IV, at point of attachment. Pencil-line margin on inside petal almost unnoticeable.

This description was made from a rose that was open for three days indoors in the month of August, 1941, at Ontario, California:

*Color.*—Outside petal: outside surface—between Hermosa Pink, Plate I, and Thulite Pink, Plate XXVI, on upper half of petal, blending gradually to near Shrimp Pink, Plate I, from the near center of the petal toward the base and lower border, which in turn changes abruptly toward point of attachment to near Martius Yellow, Plate IV. Point of attachment is near Pale Lemon Yellow, Plate IV. A very fine pencil-line margin of near Cameo Pink, Plate XXVI, may be seen bordering the upper half, more or less, of petal; inside surface—between Cameo Pink, Plate XXVI, and Thulite Pink, Plate XXVI, at tip of petal blending gradually to a slightly deeper tone of between Cameo Pink and Thulite Pink toward center, which in turn blends gradually to near Martius Yellow, Plate IV, toward base. Point of attachment near Lemon Yellow, Plate IV. Pencil-line margin of near Cameo Pink, Plate XXVI, borders both sides of the top ¾, more or less, of the petal. Inside petal: outside surface—between Thulite Pink, Plate XXVI, and Cameo Pink, Plate XXVI, on upper half of petal maintaining this color past the middle of petal where it blends gradually to near Orange Pink, Plate II, toward base, which changes abruptly first to Martius Yellow, Plate IV, and then to Pale Lemon Yellow, Plate IV, at point of attachment. Pencil-line margin of near Cameo Pink, Plate XXVI, borders both sides of the top ¾, more or less, of the petal; inside surface—between Thulite Pink, Plate XXVI, and Cameo Pink, Plate XXVI, on upper half of petal, maintaining this color past the middle of the petal where it blends gradually to near Safranto Pink, Plate II, toward base, which in turn changes abruptly first to near Martius Yellow, Plate IV, and then to near Pale Lemon Yellow, Plate IV, at point of attachment. Pencil-line margin of near Cameo Pink, Plate XXVI, borders both sides of the top ¾, more or less, of the petal.

*General color effect.*—Newly opened flower—Outer petals between Thulite Pink, Plate XXVI, and Eosine Pink, Plate I. Center between Eosine Pink, Plate I, and Begonia Rose, Plate I. Three days open—between Cameo Pink, Plate XXVI, and Thulite Pink, Plate XXVI.

*Behavior.*—Drop off cleanly.

*Flower longevity.*—On bush in garden—four to five days in August. Cut roses grown outdoors kept at living room temperatures—four to five days in August.

*Reproductive Organs*

Stamens: Medium number; arranged irregularly about pistils, mixed with some petaloids.

Filaments: Short to medium; near light cadmium, Plate IV; most with anthers.

Anthers: Medium size; open at various times; near Orange Buff, Plate III.

Pollen: Abundant; near Orange Buff, Plate III.

Pistils: Medium number.

Styles: Uneven; short to medium; medium heavy; loosely bunched.

Stigma; Near Sea Foam Green, Plate XXXI.
Ovaries: Some protruding from calyx.
Hips: Short to medium; depresso-globose; usually oblique; usually with inconspicuous neck
*Color of mature hip.*—Between Avellaneous, Plate XL, and Verona Brown, Plate XXIX, (high spots are near Avellaneous but hip is much net-veined with near Verona Brown). Smooth when immature; when mature rough walls, medium thick; fleshy.
Sepals: Permanent; medium long; slightly curled inward and recurved.
*Color.*—Inside—near Vetiver Green, Plate XLVII, at base with a sparse overlay of white tomentum. From the middle of sepal to the tip of the white tomentum becomes more predominant; however, a very faint undertone of Vetiver Green, Plate XLVII, may still be seen. Outside—near Light Elm Green, Plate XVII, changing abruptly to near Courge Green, Plate XVII, at extreme base of sepal. The denseness and placement of tomentum is variable on different sepals.
Seeds: Comparatively few; medium to large.

*Plant*

Foliage:
*Leaves.*—Pinate compound of five to seven leaflets; abundant; medium large; moderately heavy; leathery; semi-glossy.
*Leaflets.*—Broadly oval to broadly ovate; margin doubly serrate.
*Color.*—Mature: upper surface—near dark Cress Green, Plate XXXI. Base of mid-rib between Deep Sea Foam Green, Plate XXXI, and Chrysolite Green, Plate XXXI, blending gradually to near water Green, Plate XLI, at tip. Veins and net-veins near Water Green, Plate XLI; under surface—between Asphodel Green, Plate XLI, and Light Grape Green, Plate XLI. Mid-rib near Grape Green, Plate XLI, blending gradually to near Asphodel Green, Plate XLI, at tip. Veins near Asphodel Green at base blending gradually to near Pois Green, Plate XLI. Net-veins near Pois Green, Plate XLI.

Young: upper surface—near Light Hellebore Green, Plate XVII, on each side of mid-rib blending sometimes abruptly and sometimes gradually to near Neutral Red, Plate XXXVIII, toward margin. Mid-rib line is near Neutral Red at base maintaining near Neutral Red to almost the extreme tip where it changes abruptly to near Light Hellebore Green, Plate XVII. On some leaves the near Neutral Red is confined to the mid-rib line, the narrow margin line around the leaflet, and the veins; under surface—near Vetiver Green, Plate XLVII, with an overlay or blending of between Neutral Red, Plate XXXVIII, and Vinaceous-Drab, Plate XLV. Lightness or darkness of tone of overlay quite variable on different leaflets. The mid-rib at the base is between Neutral Red and Vinaceous-Drab changing gradually to near Vetiver Green, at apex and is variable as to the degree of tone in shadings and blendings. Veins are between Neutral Red and Vinaceous-Drab, some having blendings of near Vetiver Green, but the degree of tone is variable.
*Rachis (the supporting stem of the compound leaf).*—Light to medium. Upper side—grooved; hairy; glandular. Under side—hairy; sparsely prickly.
*Stipules.*—Medium long; medium wide with medium long points, turning out at an angle of more or less than 45°.
*Disease.*—Moderately resistant to mildew.
Growth:
*Habit.*—Climbing; much branched.
*Growth.*—Vigorous.
*Canes.*—Medium to heavy.
*Main stems.*—Between Hellebore Green, Plate XVII, and Rainette Green, Plate XXXI. *Large prickles*—several; medium long; some slanting and some slightly hooked downward; with medium long, broad base; between Clay Color, Plate XXIX, and Sayal Brown, Plate XXIX, changing at tip to between Sayal Brown, Plate XXIX, and Carob Brown, Plate XIV. *Small prickles*—few; between Clay Color, Plate XXIX, and Sayal Brown, Plate XXIX, changing at tip to between Sayal Brown, Plate XXIX, and Carob Brown, Plate XIV. *Hairs*—none.
*Branches.*—Between Light Cress Green, Plate XXXI, and Cress Green, Plate XXXI. *Large prickles*—several; medium long; straight; some slanting and some hooked downward; with short, broad base; between Lime Green, Plate XXXI, and Chrysolite Green, Plate XXXI, changing abruptly at tip to various shades between Clay Color, Plate XXIX, and Bister, Plate XXXIX. On the lower part of the branch the large prickles are between Mikado Brown, Plate XXIX, and Sayal Brown, Plate XXIX. *Small prickles*—few, between Lime Green, Plate XXXI, and Chrysolite Green, Plate XXXI, changing abruptly at tip to various shades between Clay Color, Plate XXIX, and Bister, Plate XXXIX. On the lower part of the branch the large prickles are between Mikado Brown, Plate XXIX, and Sayal Brown, Plate XXIX. *Hairs*—none.
*New Shoots.*—Between Light Elm Green, Plate XVII, and Rainette Green, Plate XXXI. *Large prickles*—several; medium to long; some slanting and some slightly hooked downward; with short, narrow base; between Deep Chrysolite Green, Plate XXXI, and Chrysolite Green, Plate XXXI, at tip with a faint, almost transparent, flush of near Cinnamon-Drab, Plate XLVI, toward base. *Small prickles*—few; between Deep Chrysolite Green, Plate XXXI, and Chrysolite Green, Plate XXXI, at tip with a faint, almost transparent, flush of near Cinnamon-Drab, Plate XLVI, toward base. *Hairs*—none.

I claim:

A new and distinct variety of rose plant, characterized as to novelty by its climbing habit of growth, greater floriferousness and petalage than is found in its parent grown under comparable conditions; and intermittent blooming throughout the growing season, substantially as shown and described.

HERBERT C. SWIM.